United States Patent [19]
Guay

[11] Patent Number: 5,261,901
[45] Date of Patent: Nov. 16, 1993

[54] ADJUSTABLE AND REUSABLE DIAPER

[76] Inventor: Lise Guay, 1182 route de l'Eglise, Val-Alain, Québec, Canada, G0S 3H0

[21] Appl. No.: 695,449

[22] Filed: May 3, 1991

[30] Foreign Application Priority Data

Sep. 4, 1989 [GB] United Kingdom ............. 8919893

[51] Int. Cl.⁵ .................. A61F 13/15; A61F 13/20
[52] U.S. Cl. ..................... 604/391; 604/385.1; 604/386
[58] Field of Search ............. 604/385.1, 389, 390, 604/391, 394, 400, 386, 384

[56] References Cited

U.S. PATENT DOCUMENTS

| | | | |
|---|---|---|---|
| 2,493,113 | 1/1950 | Dance | 128/287 |
| 3,141,461 | 7/1964 | Farris | 604/391 |
| 3,150,664 | 9/1964 | Noel | 604/391 |
| 3,359,980 | 12/1967 | Rosenblatt | 604/391 |
| 3,955,575 | 5/1976 | Okuda | 128/284 |
| 4,051,854 | 10/1977 | Aaron | 604/394 |
| 4,196,733 | 4/1980 | Elias-Geisseler | 128/287 |
| 4,265,245 | 5/1981 | Glassman | 128/287 |
| 4,402,690 | 9/1983 | Redfern | 604/391 |
| 4,410,327 | 10/1983 | Baggaley | 604/391 |
| 4,534,769 | 8/1985 | De Jonckheere et al. | 604/369 |
| 4,596,568 | 6/1986 | Flug | 604/369 |
| 4,681,581 | 7/1987 | Coates | 604/400 X |
| 4,704,117 | 11/1987 | Mitchell | 604/391 |
| 4,728,326 | 3/1988 | Gilles | 604/391 |
| 4,773,906 | 9/1988 | Knishel | 604/391 |
| 4,801,298 | 1/1989 | Sorenson et al. | 604/384 |
| 4,995,873 | 2/1991 | Knight | 604/391 |
| 5,100,399 | 3/1992 | Janson et al. | 604/391 X |

FOREIGN PATENT DOCUMENTS

| | | |
|---|---|---|
| 372540 | 3/1938 | Canada . |
| 523645 | 4/1966 | Canada . |
| 899552 | 5/1972 | Canada . |
| 901202 | 5/1972 | Canada . |
| 985852 | 3/1976 | Canada . |
| WO90/07313 | 7/1990 | PCT Int'l Appl. . |
| 2095561 | 10/1982 | United Kingdom . |

*Primary Examiner*—Randall L. Green
*Assistant Examiner*—Elizabeth M. Burke
*Attorney, Agent, or Firm*—Longacre & White

[57] ABSTRACT

An adjustable and reusable diaper (1) comprises an inner pad (2) made of absorbent material, and an outer panel (3) defining a front flap (15) with a first waistband portion (16) and a rear flap with a second waistband portion (18). Five Velcro strips (including 28 and 29) are respectively attached to the outer face of the first waistband portion (16) and to the inner and outer faces of the two end sections (19,12) of the second waistband portion (18). These VELCRO strips enable attachment of the first (16) and second (18) waistband portions together with the two end sections (19,20) of the second waistband portion (18) overlapping or not, whereby the diaper (1) can be easily fitted on little babies and young children having a weight ranging from about eight pounds to about thirty pounds.

12 Claims, 2 Drawing Sheets

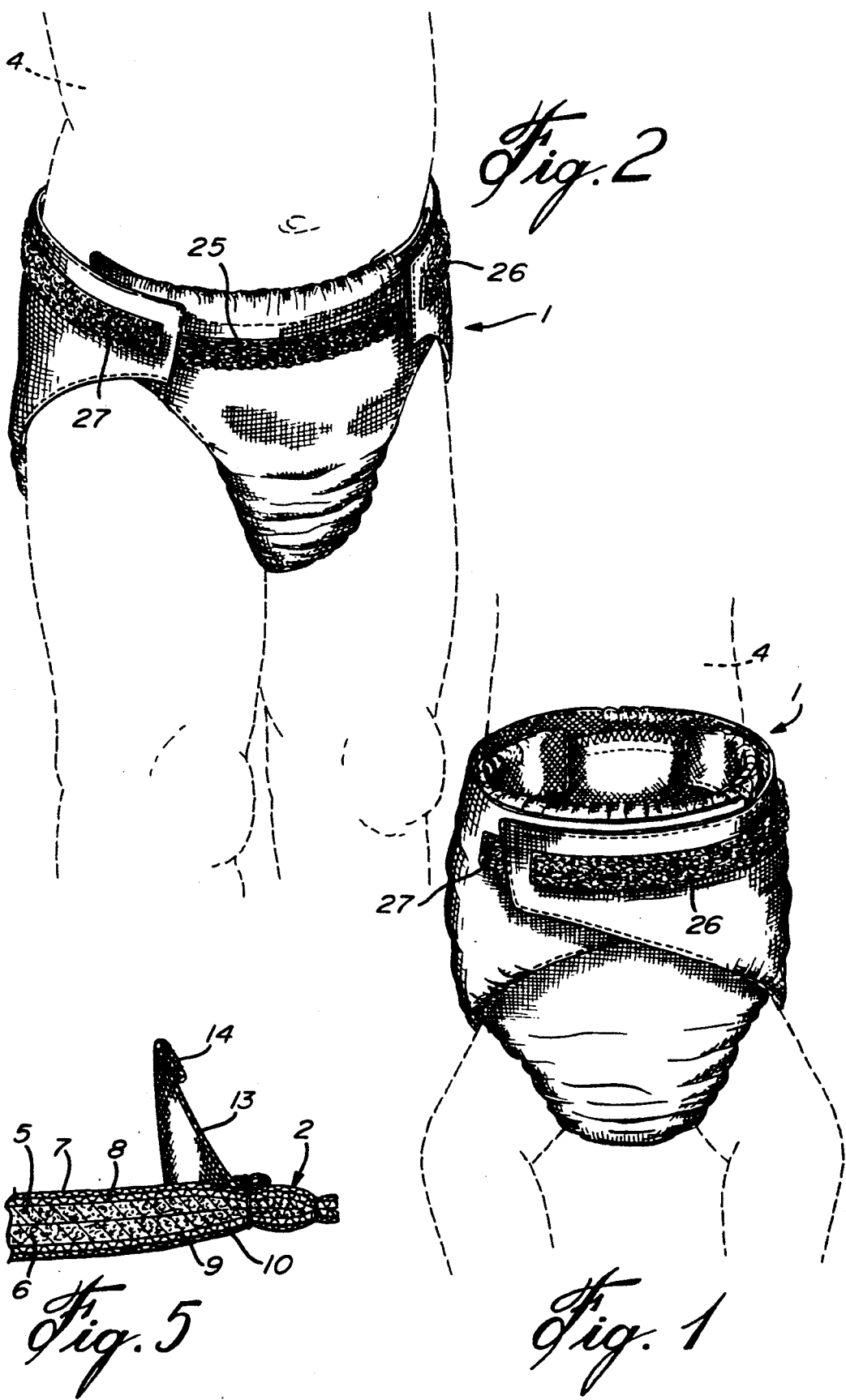

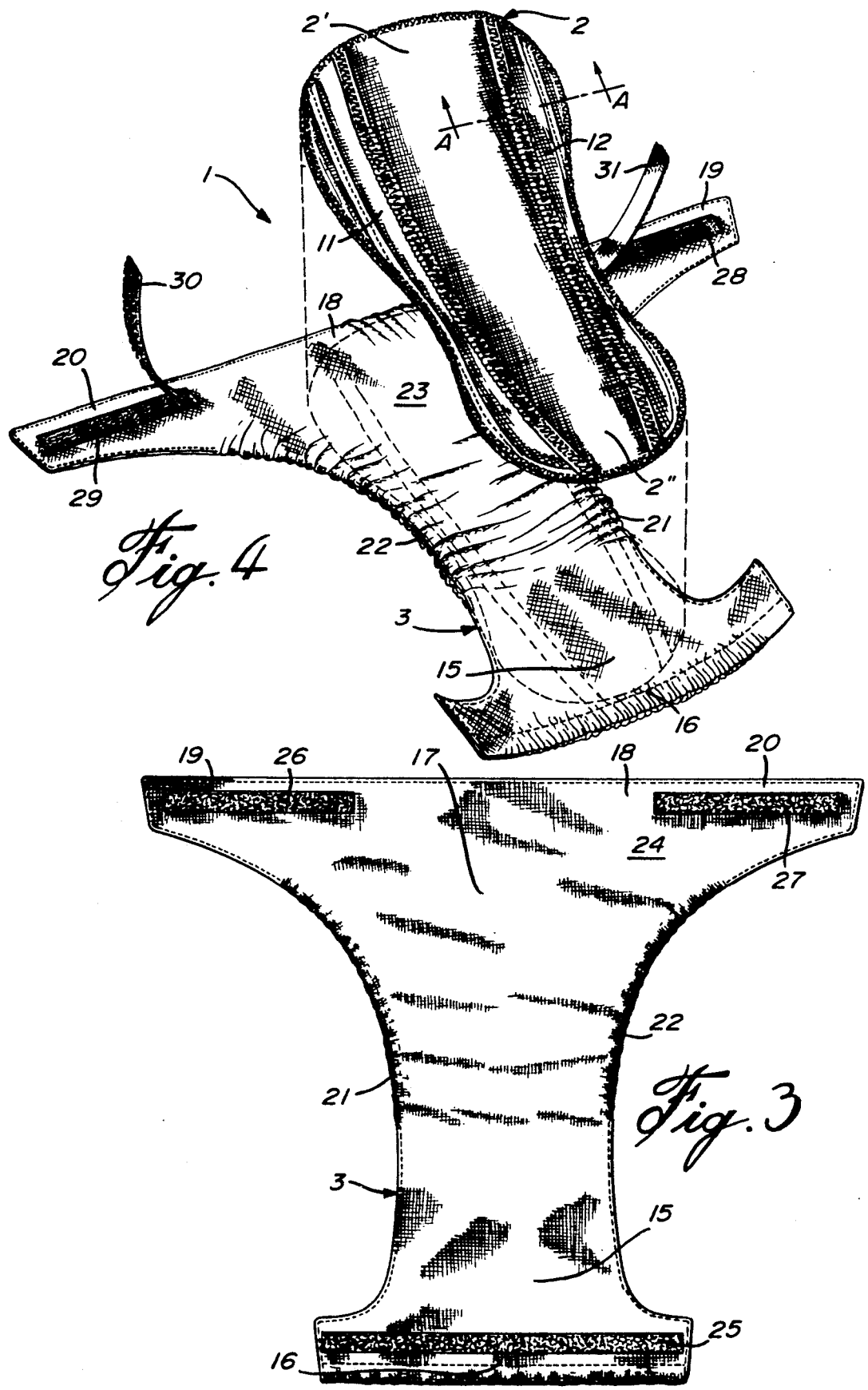

ADJUSTABLE AND REUSABLE DIAPER

BACKGROUND OF THE INVENTION

1. Field of the invention

The present invention relates to a diaper panel of which the size can be easily adjusted within a wide range of sizes. The invention also extends to a diaper comprising that panel to fit on little babies and young children having a weight ranging from about 8 lbs to about 30 lbs.

2. Brief description of the prior art

Many adjustable and reusable diapers have been proposed in the prior art. Some examples are described and illustrated in the following U.S. Pat. Nos.:

4,402,690 (Redfern) issued on Sep. 6, 1983;
4,704,117 granted to Mitchell on Nov. 3, 1987;
4,773,906 granted to Krushel on Sep. 27, 1988; and
4,801,298 (Sorenson et al.) issued on Jan. 31, 1989.

In particular, Krushel proposes a diaper comprising an outer panel defining a front flap with a first waistband portion and a rear flap with a second waistband portion. On the outer face of the first waistband portion is secured at least one VELCRO (trademark) loop fabric strip. The second waistband defines two end arms with inner faces on which VELCRO hook tabs are secured. In operation, the position of the hook tabs on the VELCRO strip is adjusted to fit the diaper on the baby or young child. An additional VELCRO loop tab is also secured on the outer face of one of the two end arms. This enables overlapping of these two end arms with an inner hook tab of the opposite end arm engaged with this additional tab to lock the so overlapped arms.

In general, adjustment of the size of the prior art reusable diapers is limited as they do not enable significative reduction of diaper size while the two end sections of the waistband portion of the rear flap are overlapped.

OBJECT OF THE INVENTION

An object of the present invention is therefore to eliminate the above discussed drawback of the prior art by providing a diaper panel, and accordingly a diaper comprising that panel, of which the size can be adjusted within a wide range of sizes while the two end sections of the waistband portion of the rear panel flap are overlapped.

SUMMARY OF THE INVENTION

In accordance with the present invention, there is provided an adjustable and reusable diaper panel defining front and rear flaps, the front flap including a first waistband portion with an outer face, and the rear flap including a second waistband portion with inner and outer faces and first and second end sections. The improvement in the diaper panel comprises first fastener means distributed along the first waistband portion on the outer face thereof, second and third fastener means on the inner face of the first and second end sections of the second waistband portion, respectively, and fourth fastener means extending along the second waistband portion on the outer face of the above mentioned first end section. The second and third fastener means are attachable to the first fastener means at a plurality of different positions along the first waistband portion, while the third fastener means is attachable to the fourth fastener means at a plurality of different positions along the second waistband portion. The size of the diaper panel can accordingly be adjusted within a wide range of sizes by adjusting (a) the position of the second and third fastener means on the first fastener means with the first and second end sections of the second waistband portion not overlapping each other, or (b) the position of the second fastener means on the first fastener means and the position of the third fastener means on the first and/or fourth fastener means with the second end section of the second waistband portion overlapping the first end section thereof.

In accordance with a preferred embodiment of the present invention, the diaper panel further comprises fifth fastener means distributed along the second waistband portion on the outer face of the above mentioned second end section, the second fastener means being attachable to the fifth fastener means at a plurality of different positions along the second waistband portion. The size of the diaper panel can then also be adjusted by adjusting the position of the third fastener means on the first fastener means and the position of the second fastener means on the first and/or fifth fastener means with the first end section of the second waistband portion overlapping the second end section thereof.

Advantageously, the first, second, third fourth and fifth fastener means comprise VELCRO strips. In the present specification and in the appended claims, the term "VELCRO" is meant to designate loop and hook fabric strips commercialized under the trademark VELCRO or any equivalent.

The present invention further relates to an adjustable and reusable diaper comprising the above described diaper panel.

The objects, advantages and other features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 1 shows a small baby of about 8 lbs wearing a diaper in accordance with the present invention;

FIG. 2 shows a young child of about 30 lbs wearing the diaper of FIG. 1;

FIG. 3 illustrates the outer face of an outer panel of the diaper of FIGS. 1 and 2;

FIG. 4 illustrates the inner face of the diaper panel of FIG. 3 and the pad, made of absorbent material, placed on the inner face of this panel; and FIG. 5 is a cross sectional view of the absorbent pad of FIG. 4 taken along axis A—A.

DETAILED DESCRIPTION OF THE PREFERRED EMBODIMENT

Referring now to FIGS. 1 to 5 of the appended drawings, the diaper in accordance with the present invention, generally identified by the reference numeral 1, comprises an inner pad 2 and an outer panel 3.

The pad 2 is not attached to the outer panel 3 and is therefore removable to be washed separately. More specifically, the pad 2 is only disposed on the inner face of the outer panel 3 before fitting the diaper on the baby or young child 4.

Although its rear flap 2' is wider than its front flap 2'', the pad 2 presents the general shape of an hourglass to closely adapt the contour of the body of the baby or young child 4. Indeed, the central portion of the pad 2 contours the body between the legs while its rear and front flaps 2' and 2" are wide enough to adequately cover the posterior and front of the body of the baby or young child 4.

The pad 2 is obviously made of absorbent material including for example two layers 5 and 6 of absorbent fabric such as felt and four layers 7, 8, 9 and 10 of flannelette (see FIG. 5).

The pad 2 may also be formed, when desired, with a pair of lateral leakage resistant elastic flanges 11 and 12. These flanges 11 and 12 are each made of a layer of flannelette or of any other suitable fabric material such as 13 (FIG. 5) sewed to the corresponding lateral edge of the pad 2 and of an elastic webbing 14 sewed to the free edge of the layer 13. The webbings 14 apply the free edges of the flanges 11 and 12 on the skin of the baby or young child 4. The material of the flanges 11 and 12 can obviously be selected to obtain the best protection against lateral leakage. It should be pointed out here that the flanges 11 and 12 may be of various lengths.

The outer panel 3 defines a front flared flap 15 (FIGS. 3 and 4) including a waistband portion 16, and a rear flap 17 including a waistband portion 18. The two end sections 19 and 20 of the waistband portion 18 define a pair of arms identified by the same reference numerals 19 and 20. The panel 3 further defines lateral concave edges 21 and 22 to receive the legs of the baby or young child 4. Elastic webbings are advantageously sewed to the waistband portion 16, to the central section of the waistband portion 18 and to the concave edges 21 and 22 to better fit the panel 3 on the body of the baby or young child 4. In particular, these elastic webbings prevent leakage through the space between the lateral edges 21 and 22 and the skin of the baby or young child 4.

The panel 3 is formed of an outer layer 24 of impermeable material, an intermediate layer (not shown) of flannelette and an inner layer 23 also made of flannelette. The material of the layer 24 may comprise fully impermeable nylon or a fabric which is impermeable to liquid but permeable to air. The latter fabric is advantageous in that it enables aeration through the diaper panel 3. Obviously, other materials can be envisaged for manufacturing the latter panel. For example, the intermediate and inner layers of flannelette can be replaced by a net fabric or else to meet the requirements of institutions such as hospitals.

On the outer face of the waistband portion 16 is sewed a VELCRO loop fabric strip 25. Also, a VELCRO loop fabric strip 26 is sewed on the outer face of the end section 19 of the waistband portion 18, while a VELCRO loop fabric strip 27 is sewed to the outer face of the end section 20 of the waistband portion 18. Finally, a VELCRO hook fabric strip 28 is sewed to the inner face of the end section 19 of the waistband portion 18 and another VELCRO hook fabric strip 29 is sewed to the inner face of the end section 20 of the waistband portion 18. Accordingly, the strip 25 extends along the waistband portion 16 while the strips 26, 27, 28 and 29 extend along the waistband portion 18.

As can be appreciated, the strip 28' can be attached to the strip 25 at a plurality of different positions along the waistband portion 16 and also to the strip 27 at a plurality of different positions along the waistband portion 18. Regarding strip 29, it can be attached to the strip 25 at a plurality of different positions along the waistband portion 16 and also to the strip 26 at a plurality of different positions along the waistband portion 18.

Two VELCRO loop fabric strips 30 and 31 each have one end sewed to the panel 3 at a corresponding end of the strips 29 and 28, respectively. The strips 30 and 31 are applied to the strips 29 and 28 to prevent the latter strips to catch shreds during washing and drying of the panel 3, and also to prevent different panels 3 to attach to each other in the washing and drying machines.

In order to fit the diaper 1 on a baby or young child, the pad 2 is first disposed on the inner face of the panel 3. The diaper 1 is then placed on the baby or young child 4 with the concave edges 21 and 22 receiving his legs. The front flap 15 is positioned on the front of his body and the rear flap 17 on his posterior. His waist is then surrounded by the end sections 19 and 20 of the waistband portion 18.

In the case of a relatively tall young child (FIG. 2), the diaper 1 is attached around his waist by engaging the hook strips 28 and 29 with the loop strip 25, with the end sections 19 and 20 not overlapping each other. The positions of the strips 28 and 29 on the strip 25 are selected to comfortably fit the diaper 1 around the waist of the child 4.

In the case of a small baby (FIG. 1), the diaper 1 is fitted on his waist by engaging the hook strip 29 with the loop strip 25 and by subsequently engaging the hook strip 28 with the loop strip 27. Another alternative (not shown) is to engage the strip 28 with the strip 25 and to subsequently engage the strip 29 with the loop strip 26. The diaper 1 can therefore be comfortably fitted on a small baby both easily and rapidly by left-handed or right-handed parents.

In the case of a taller baby, the strip 28 can engage both the strips 25 and 27 to fit the diaper 1 on the baby 4. Alternatively, the strip 29 can engage both the strips 25 and 26.

A diaper in accordance with the present invention can be dimensioned to fit on babies and young children having a weight ranging from about 8 lbs to about 30 lbs. Normally, when a child reaches a weight of about 30 lbs, the period during which he wears diapers will end.

A diaper in accordance with the present invention can also be dimensioned to fit on adolescents and adults suffering for example from incontinence.

The diaper in accordance with the invention presents, amongst others, the following additional advantages:

as the outer panel 3 is attached in front of the diaper 1, (a) the surface on which the back of the baby or young child 4 rests upon changing the diaper cannot be soiled, and (b) a young child can detach and remove himself the diaper when the is tall enough to commence to go to the toilet alone; and as the panel 3 and the pad 2 constitute two separate pieces, (a) drying of the diaper 1 is faster, (b) the pad 2 can be chlorinated when needed without damaging the panel 3, and (c) when the child is tall enough to commence to go to the toilet alone, the pad 2 can be removed and upon an accident, the liquid will be absorbed by the intermediate and inner layers of flannelette and retained by the impermeable outer layer of the panel 3 to prevent wetting of the clothes of the child.

Although the present invention has been described hereinabove by way of a preferred embodiment thereof, such an embodiment can be modified at will, within the scope of the appended claims, without departing from the spirit and nature of the subject invention. For example, the VELCRO strips can be replaced by snap fasteners distributed along the waistband portions 16 and 18. Also, the Velcro loop fabric strips can be replaced by the outer layer of the panel 3 formed of a fabric that can be engaged with the VELCRO hook fabric strips 28 and 29.

We claim:

1. An adjustable and reusable diaper panel comprising:
   a pair of interconnected front and rear flaps said front flap including a front waistband portion having an outer face and a length, and said rear flap including a rear waistband portion having inner and outer faces and first and second opposite end sections;
   first elongated fastener means extending along said front waistband portion on the outer face thereof;
   second fastener means on the inner face of said first end section of the rear waistband portion, said second fastener means being so attachable to the firs fastener means as to enable longitudinal adjustment of a position of said second fastener means on said first elongated fastener means;
   third fastener means on the inner face of said second end section of the rear waistband portion, said third fastener means being so attachable to the first fastener means as to enable longitudinal adjustment of a position of said third fastener means on said first elongated fastener means;
   fourth elongated fastener means extending along said rear waistband portion on the outer face of said first end section, said third fastener means being so attachable to the fourth fastener means as to enable longitudinal adjustment of a position of the third fastener means on said fourth elongated fastener means; whereby size of the diaper panel can be adjusted within a wide range of sizes by adjusting longitudinally (a) the position of said second and third fastener means on said first elongated fastener means with the first and second end sections of the rear waistband portion not overlapping each other, or (b) the position of the second fastener means on the first elongated fastener means and the position of the third fastener means on the fourth elongated fastener means with said second end section of the rear waistband portion overlapping said first and section.

2. An adjustable and reusable diaper panel as defined in claim 1, in which said first, second, third and fourth fastener means comprise VELCRO strips.

3. An adjustable and reusable diaper panel as defined in claim 13, further comprising a fifth elongate fastener means extending along the rear waistband portion on the outer face of said second end section, said second fastener means being so attachable to the fifth fastener means as to enable longitudinal adjustment of the second fastener means on said fifth elongated fastener means, whereby the size of the diaper panel can also be adjusted by adjusting longitudinally a position of the third fastener means on the first elongated fastener means and a position of the second fastener means on the fifth elongated fastener means with the first end section of the rear waistband portion overlapping the second end section thereof.

4. An adjustable and reusable diaper panel as defined in claim 3, in which said second and third fastener means comprise VELCRO hook fabric strips and said first, fourth and fifth elongated fastener means comprise VELCRO loop fabric strips.

5. An adjustable and reusable diaper panel as defined in claim 1, wherein said first elongated fastener means extend substantially over the length of said front waistband portion.

6. An adjustable and reusable diaper panel as defined in claim 1 wherein said second and third fastener means are elongated and extend along said rear waistband portion on the inner face of said first and second end sections, respectively.

7. An adjustable and reusable diaper comprising:
   an inner pad means made of absorbent material
   an outer diaper panel having an inner side to receive said pad means, and a pair of interconnected front and rear flaps, said front flap including a front waistband portion with an outer face and a length, and said rear flap including a rear waistband portion with inner and outer faces and with first and second opposite end sections;
   first elongated fastener means extending along said front waistband portion on the outer face thereof;
   second fastener means on the inner face of said firs end section of the rear waistband portion, said second fastener means being so attachable to the first fastener means as to enable longitudinal adjustment of a position of the second fastener means on id first elongated fastener means;
   third fastener means on the inner face of said second end section of the rear waistband portion, said third fastener means being so attachable to the first fastener means as to enable longitudinal adjustment of the position of the third fastener means on said first elongated fastener means;
   fourth elongated fastener means extending along said rear waistband portion on the outer face of said first end section, said third fastener means being so attachable to the founts fastener means as to enable longitudinal adjustment of the third fastener means on said fourth elongated fastener means; whereby size of the diaper can be adjusted within a wise range of sizes by adjusting longitudinally (a) the position of said second and third fastener means on said first elongated fastener means with the first and second end sections of the rear waistband portion not overlapping each other, or (b) the position of the second fastener means on the first elongated fastener means and the position of the third fastener means on the fourth elongated fastener means with said second end section of the rear waistband portion overlapping said first end section.

8. An adjustable and reusable diaper as defined in claim 7, in which said first, second, third and fourth fastener mean comprise VECLRO strips.

9. An adjustable and reusable diaper as defined in claim 7, further comprising a fifth elongated fastener means extending along the rear waistband portion of the outer face of said second end section, said second fastener means being so attachable to the fifth fastener means as to enable longitudinal adjustment of the second fastener means on said fifth elongated fastener means, whereby the size of the diaper panel can also be adjusted by adjusting longitudinally a position of the third fastener means on the first elongated fastener means and a position of the second fastener means on the fifth elongated fastener means with the first end section of the rear waistband portion overlapping the second end section thereof.

10. An adjustable and reusable diaper as defined in claim 9, in which said second and third fastener means comprise VECLRO hook fabric strips and said first, fourth and fifth elongated fastener means comprise VELCRO loop fabric strips.

11. An adjustable and reusable diaper as defined n claim 7, wherein said first elongated fastener means extend substantially over the length of said front waistband portion.

12. An adjustable and reusable diaper as defined in claim 7, wherein said second and third fastener means are elongated and extend along said rear waistband portion on the inner face of said first and second end sections, respectively.

* * * * *